United States Patent [19]

Green et al.

[11] Patent Number: 5,074,306

[45] Date of Patent: Dec. 24, 1991

[54] MEASUREMENT OF BURN DEPTH IN SKIN

[75] Inventors: Howard A. Green, West Roxbury; John A. Parrish; Richard R. Anderson, both of Boston, all of Mass.

[73] Assignee: The General Hospital Corporation, Boston, Mass.

[21] Appl. No.: 483,907

[22] Filed: Feb. 22, 1990

[51] Int. Cl.$^5$ ............................................. A61B 5/00
[52] U.S. Cl. ..................... 128/664; 128/633
[58] Field of Search ................. 128/633, 664, 665; 606/9

[56] References Cited

U.S. PATENT DOCUMENTS

| | | | |
|---|---|---|---|
| 4,170,987 | 10/1979 | Anselmo et al. | 128/665 |
| 4,469,098 | 9/1984 | Davi | 128/395 |
| 4,608,990 | 9/1986 | Elings | 128/633 |
| 4,693,255 | 9/1987 | Beall | 128/665 |
| 4,718,416 | 1/1988 | Nanaumi | 606/9 |
| 4,938,224 | 7/1990 | Rysavy | 128/633 |

OTHER PUBLICATIONS

Black et al., The Journal of Burn Care Rehabilitation "Burn Death Evaluation with Fluorometry: is it really definitive?" (Abstract), vol. 7, No. 4, pp. 313–317 (Jul.-Aug.).
Gregory S. Van Liew, Martin A. Afromowitz, "Clinical Evaluation of Burn Injuries using an Optical Relectance Technique", IEEE Trans. On Biomedical Engineering, vol. BME-34, No. 2, (Feb. 1987), pp. 114–127.
Martin A. Afromowitz, et al. "Multipectral Imaging of Burn Wounds: A New Clinical Instrument for Evaluating Burn Depth", IEEE Trans. Biomed. Eng., vol. 35, No. 10, (Oct. 1988) pp. 842–850.
John E. Gatti, M.D. et al., "Evaluation of the Burn Wound with Perfusion Fluorometry", *The Journal of Trauma*, vol. 23, No. 3, pp. 202–206, (Sep. 9–11, 1982).
Diversatronics, Inc., "A Breakthrough for Monitoring Nutritive Blood Flow", pp. 1–4.
Howard A. Green, M.D., "Dual Wavelength Excitation of Indocyanine Green Fluorescence to Determine Burn Depth", American Burn Assn. Conference Abstract, Mar. 27–30, 1990.
G. Moneta et al., "Infrared Fluorescence Videomicroscopy of Skin Capillaries with Indocyanine Green", Int. J. Microcirc: Clin. Exp. 6:25–34 (1987), pp. 25–34.
Flower, R. W., et al., "Indocyanine Green Dye Fluorescence and Infrared Absorption Choroidal Angiography Performed Simultaneously with Fluorescein Angiography", Johns Hopkins Medical Journal 138, pp. 33–42, (1976).
Howard A. Green, M.D., et al., "Mid-Dermal Wound Healing: A Comparison Between Excision with a Dermatome and Pulsed Carbon Dioxide ($CO_2$) Laser", Pub. American Burn Assocation Meeting, Abstract, Mar. 27–30, 1990.
Howard A. Green, M.D., et al., "Pulsed Carbon Dioxide ($CO_2$) Laser Ablation of Burn Eschar: In Vitro and In Vivo Analysis", Pub. American Burn Assocation, Abstract, Mar. 27–30, 1990.

(List continued on next page.)

*Primary Examiner*—Lee S. Cohen
*Assistant Examiner*—K. M. Pfaffle
*Attorney, Agent, or Firm*—Fish & Richardson

[57] ABSTRACT

A method for distinguishing between a full thickness and a partial thickness skin burn in a patient having a skin burn. The methods includes administering a fluorescent compound, which is excited by infrared light, to the patient to cause the compound to enter one or more capillaries below and adjacent the skin burn. The compound is then excited with infrared light, and the amount of fluorescence of the compound caused by the infrared light detected at the skin burn and at unburned skin adjacent the skin burn. The ratio of fluorescence detected at the skin burn and at the unburned skin is an indication of the thickness of the skin burn, e.g., a ratio of less than 0.4 indicates a full thickness skin burn.

14 Claims, 6 Drawing Sheets

Green et al., The Journal of Investigative Dermatology, vol. 92, No. 3, Mar. 1989, "Skin Graft Take and Healing After $CO_2$ and 193 nm Excimer Laser Ablation of Graft Beds".

Abergel et al., "Aging Hands: A Technique of Hand Rejuvenation by Laser Resurfacing and Autologous Fat Transfer", J. Dermatol Surg., Jul. 1989, pp. 725-728.

Abergel et al., "Laser Abrasion for Cosmetic and Medical Treatment of Facial Actinic Damage", vol. 43, Jun. 1989, pp. 583-587.

Walsh et al., "Pulsed $CO_2$ Laser Tissue Ablation: Effect of Tissue Type and Pulse Duration on Thermal Damage", 1988 Alan R. Liss, Inc., pp. 109-118, Lasers in Surgery and Medicine 8:108-118.

Ben-Baruch et al., "Comparison of Wound Healing Between Chopped Mode-Superpulse Mode $CO_2$ Laser and Steel Knife Incision", Lasers in Surgery and Medicine 8:596-599 (1988).

Lanzafame et al., "Comparison of Continuous-Wave, Chop-Wave, and Super Pulse Laser Wounds", Laser in Surgery and Medicine 8:119-124 (1988).

Fleming et al., "Skin-edge Necrosis in Irradiated Tissue after Carbon Dioxide Laser Excision of Tumor", Lasers in Medical Science (1986), pp. 264-265, (Apr. 29, 1986).

Badawy et al., "Comparative study of continuous and pulsed $CO_2$ laser on tissue healing and fertility outcome in tubal anastomosis", vol. 47, No. 5, May 1987.

Baggish et al., "Comparison of electronically superpulsed and continuous-wave $CO_2$ laser on the rat uterine horn*", vol. 45, No. 1, (1986).

MEASUREMENT OF BURN DEPTH IN SKIN

BACKGROUND OF THE INVENTION

This invention relates to methods and apparatus for determination of burn depth in skin, and for removing burnt skin.

Afromowitz et al., (BME-34 IEEE Transactions on Biomedical Engineering 114, 1987; Afromowitz et al., 35 IEEE Transactions on Biomedical Engineering 842, 1988) describe a real-time video imaging system for analysis of debrided burn wounds on the third day after burning. The relative diffuse reflectivity of the burn wound is measured in the red, green, and near infrared wavelength bands; these measurements are used to determine the probability of tissue healing.

Gatti et al., (23 J. Trauma 202, 1983) describe use of sodium fluorescein to determine the depth of a burn. The rate of fluorescein uptake and burn wound fluorescence is compared to that of normal unburned skin. Their results suggest that no distinction can be made between superficial and deep partial thickness burns.

Diversatronics (Advertisement) describes the fiber-optic perfusion fluorometer used by Gatti et al., supra.

SUMMARY OF THE INVENTION

The present invention features a method by which burn depth in skin can be assessed at an early time after burning. This method allows differentiation of burns which will not heal completely within two weeks (full thickness or deep dermal burns), and thus will need excision and grafting therapy, from burns which will heal in two weeks (partial thickness burns), and therefore, do not need to be surgically excised and grafted. The method allows accurate prediction of burn depth within a few hours after a burn. The method is thus useful for guiding a surgeon or laser in debriding burn eschar and necrotic tissue.

Unlike prior methods, the resolution of the method of this invention is sufficient to allow debridement of eschar to within a few microns of viable tissue below the burned tissue. Simultaneous use of this method with a pulsed $CO_2$ laser allows precise removal of the eschar with a minimum amount of blood loss to the patient. Prior methods for intraoperative detection of viable tissue necessitated removal of eschar until bleeding occurred. Such bleeding is detrimental to a patient, especially when that patient has a significant percentage of skin burn.

In a first aspect, the invention features a method for determining the thickness of a skin burn, and thus distinguishing between a full thickness and a partial thickness skin burn in a patient. The method includes administering a fluorescent compound, which is excitable by infrared light (ranging from 700-12,000 nm, preferably 700-1500 nm), to the patient to cause the compound to enter one or more capillaries below and adjacent the skin burn. The compound is then excited with infrared light, and the amount of fluorescence of the compound caused by the infrared light detected at the skin burn and at unburned skin adjacent the skin burn. The ratio of fluorescence detected at the skin burn and at the unburned skin is an indication of the thickness of the skin burn, e.g., a ratio of greater than 0.4, preferably more than 1.0 or 2.0, indicates a full thickness skin burn.

In preferred embodiments, the method also includes detecting the amount of fluorescence caused by the infrared light at the skin burn and at the unburned skin adjacent the skin burn prior to administering the fluorescent compound. These levels of fluorescence are then subtracted from those levels of fluorescence detected after administering the fluorescent compound, prior to calculating the ratio of the levels of fluorescence of the compound.

In other preferred embodiments, the method also includes administering a second fluorescent compound, which may be the same as the above fluorescent compound, which is excitable by ultraviolet light (ranging from 200–400 nm), to the patient to cause the second fluorescent compound to enter one or more capillaries below and adjacent the skin burn. This second fluorescent compound is then excited with ultraviolet light, and the amount of fluorescence of the second fluorescence compound caused by the ultraviolet light detected at the skin burn and at unburned skin adjacent the skin burn. The ratio of fluorescence of the compound at the skin burn and at the unburned skin is an indication of the depth of the skin burn.

In the more preferred embodiments, the fluorescent compounds emit light in the infrared region when excited; both fluorescent compounds are indocyanine green, or the fluorescent compound is indocyanine green, and the second fluorescent compound is fluorescein; the ratio of fluorescence of the fluorescent compound and the second fluorescent compound in response to the infrared and ultraviolet light, respectively, is indicative of the depth of the skin burn; the amount of fluorescent compound is measured with a dual wavelength fluorescent video imaging processing system; and the skin burn tissue is removed after detecting the amount of fluorescence, and the amount of fluorescence then again detected after such removal; even more preferably the removal involves excising the skin burn tissue with a pulsed $CO_2$ laser.

The use of a fluorescent dye which is excited by infrared light is significantly advantageous over use of a dye excited only by ultraviolet light. Infrared light is minimally interfered with by the major skin and burn chromophores (blood, melanin, and carotenoids). Thus, the overlying skin or burn eschar is almost transparent to such light; and the depth of penetration of infrared light in burn eschar is significantly greater than that of ultraviolet light. Similarly, use of a dye which fluoresces in the infrared region allows minimal interference by the major skin and burn chromophores with detection of such fluorescence. Thus, such a dye allows deeper penetration and more accurate detection of viable tissue. When such a fluorescent compound is used in combination with a compound which fluoresces in response to ultraviolet light, especially when it fluoresces in the infrared region, the simultaneous excitation with infrared and ultraviolet light allows viable tissue to be measured at two depths. This dual wavelength excitation allows a surgeon with a knife or a laser to remove necrotic tissue from the burn surface and assess the remaining tissue circulation at both shallow (100 microns) and deep (1.2 mm) distances below the cutting surface. This allows a surgeon to cease removal of overlying necrotic tissue just prior to reaching viable or regenerating skin. Thus, conservative eschar removal with preservation of underlying vital tissue is achieved.

Indocyanine green is a preferred embodiment of the invention since it has the ideal properties of fluorescing in the infrared region in response to both ultraviolet and infrared exciting light wavelengths. Thus, this single dye can be used to assess burn depth with two types of light. Supplementation of the use of indocyanine green with sodium fluorescein allows even greater accuracy in assessing the depth of burn tissue.

This early differentiation of full from partial thickness burns enables a burn surgeon (or even a laser guided by the video image produced by the above method) to diagnose and therefore perform early excision grafting of full thickness burns. This decreases morbidity and mortality.

In a second aspect, the invention features a method for precise ablative excision of burnt tissue. The method involves providing a pulsed $CO_2$ laser with a pulse width of less than 200 msec and a repetition rate of delivery of fewer than 50 (preferably fewer than 40) pulses per second to one spot; and causing laser light from the pulsed $CO_2$ laser to contact, and thus excise, the burnt tissue.

In preferred embodiments, the pulsed laser light is provided with a radiant exposure of between 5.0 and 19 joules/cm$^2$, and at least 0.5 cm$^2$, preferably 1 cm$^2$, of burnt tissue is excised.

Applicants have discovered that a pulsed $CO_2$ laser, with the above pulse specifications, is an ideal tool for removal of eschar from skin burns. Use of a short pulse of laser energy allows removal of tissue efficiently and precisely with limited concurrent thermal damage to underlying tissue. The residual zone of thermal damage of the pulsed $CO_2$ laser does not inhibit split thickness graft take or healing. With visual feedback, laser ablation can be stopped within a few microns of viable underlying muscle fascia. When this procedure is combined with the above burn depth imaging device the burn eschar can be removed with great accuracy without damaging underlying viable tissue. Such excision is far superior to use of mechanical tools, or other medical lasers.

The above laser is ideal for excisions, that is, the removal of at least 0.5 cm$^2$ of tissue. The laser is ideal because it causes hemostasis; it guickly and efficiently removes dead skin, while leaving viable remaining tissue intact; and it allows precise control of the depth of excisions.

Other features and advantages of the invention will be apparent from the following description of the preferred embodiments, and from the claims.

DESCRIPTION OF THE PREFERRED EMBODIMENTS

The drawings will first briefly be described.

DRAWINGS

STRUCTURE

Video Imaging System

Figure 1:
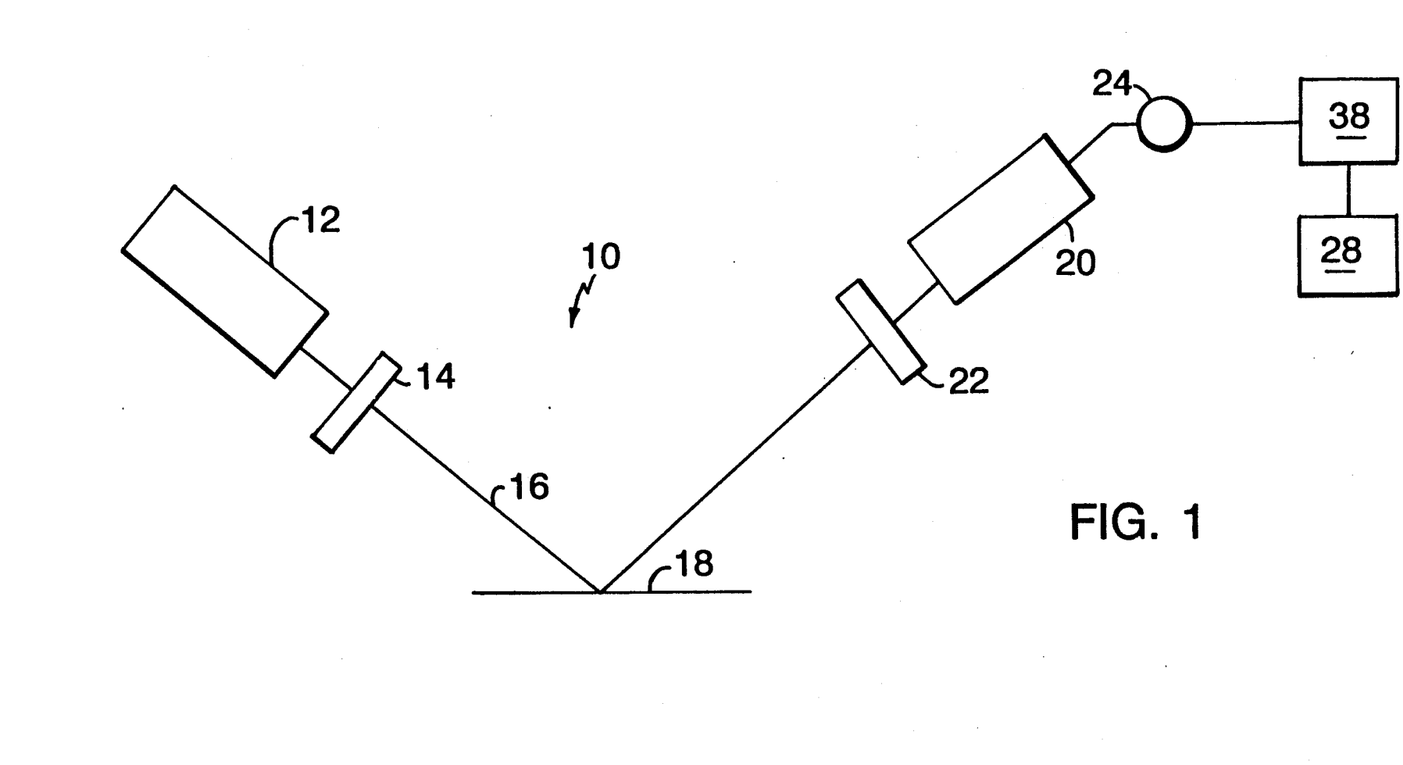
FIG. 1 is a diagrammatic representation of a dual wavelength infrared fluorescence video imaging system.
Figure 2:
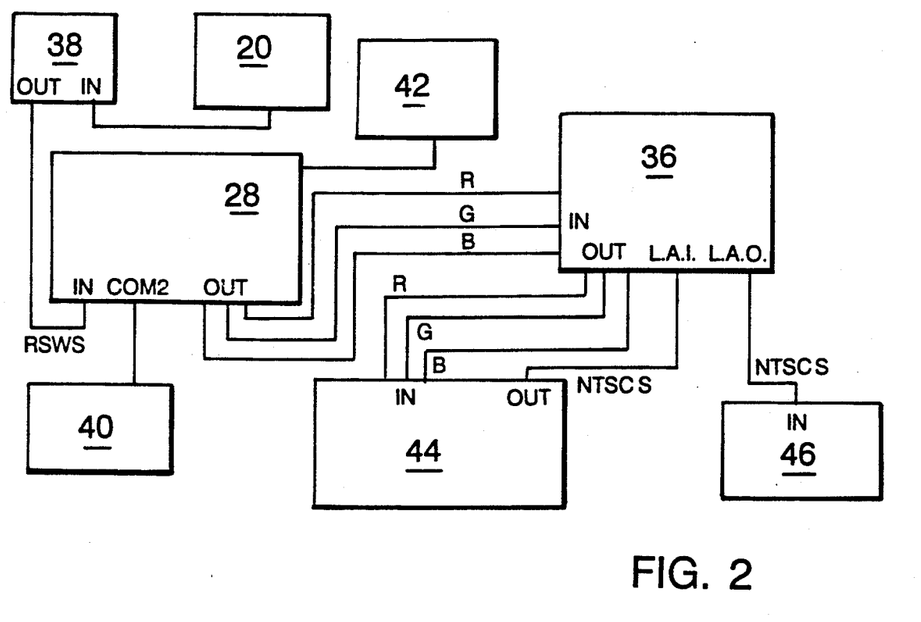
FIG. 2 is a circuit diagram of an image processing system.

Referring to Figs. 1 and 2, there is shown in diagrammatic form the general structure of an image processing system for use in the method of this invention. Video imaging system 10 is provided with an excitation light source 12 chosen from continuous wave xenon or mercury lamps (ILC Technology) or a pulsed xenon lamp (EG&G Industries). In one embodiment, the light source is an International Light Corporation Ceermax Xenon Lamp CX300 UV which provides broad spectrum excitation radiation to fluoresce the target and its vital dye either in the UV, visible, or infrared (IR) spectrum. The light from this source is caused to pass through excitation filters 14. These filters select excitation radiation wavelengths for fluorescence image capture and quantification analysis via the CCD or ICCD camera and major computer system. These are interchangeable variable filters for exciting both fluorescein and indocyanine green dyes in the visible, ultraviolet and infrared regions of the light spectrum. For example, a narrow band interference filter at either 805 or 380 nanometers (Esco Industries), a long pass 710 nanometers filter or short pass 450 nanometers filter (Corion, Inc.), or an 850 nanometers narrow band interference filter (Esco Industries) may be used. The band width of these excitations filters may vary from 5 to 40 nanometers, with the optimal center band excitation wavelengths being chosen as follows: fluorescein excitation: 490 nanometers; indocyanine green (UV excitation): 400 nanometers; and indocyanine green (infrared excitation): 780 nanometers. The filtered light may also be delivered as a beam or through a fiber 16, for example, a bifurcated round bundled silica fiber (Fiberguide Industries) to a target 18, for example, burned or unburned skin.

The fluorescent radiation of the target is detected by a camera 20, which is an image intensified CCD camera (ICCD) manufactured by Clifftondale Electronics, Inc., Model #FT450 with 100 times more sensitivity than the CCD camera, customized for gain control. This camera captures selected fluorescing photons. Each pixel or photon capturing detector in the camera stores the emission photon energy, and converts it to electrical current of a corresponding intensity. Prior to detection by the camera, the light is caused to pass through barrier filters 22 which are interchangeable variable emission filters designed to select the fluorescing radiation from the tissue, caused by fluorescence of indocyanine green or fluorescein dyes, in the visible and infrared regions of the spectrum. Band widths of these barrier filters may vary from 5 to 40 nanometers with optimal center band emission barrier filter wavelengths as follows: fluorescein fluorescence: 550 nanometers, indocyanine green fluorescence (uv excitation): 840 nanometers, and indocyanine green fluorescence (infrared excitation): 850 nanometers. Other filters from other filter manufacturers, for example, Melles Griot, Schott, and Omega Corporations, may be used. For example, the Esco #5-92-8400 (840 nm) is used for infrared fluorescence from either UV or IR excitation of indocyanine green in target skin; Corlon S-10-560S is used for visible fluorescence from fluorescein.

The light detected by the camera is intensified by an image intensifier 24. Information from the image intensifier is passed to various electronic components including a major computer 28, and a monitor 38, for analysis by standard technique.

Computer 28 is a Unitech Thinkmate 386-based IBM compatible with an 80 megabit hard drive, a data translation video frame grabber board (#2862-60) which converts the electrical output from the video camera to a digital signal which can be used by the computer; and Imagepro II (Media Cybernetics Co.), a standard image processing software adapted for use in this application. This is a comprehensive image processing software package designed for microcomputers. Image Pro II clarifies images, removes haze, improves contrast, outlines edges, zooms in to study detail, and changes light intensity to help read information hidden to the human eye; it also performs analysis and enhancement functions, including filtering operations to detect edges and outlines, contrast management, and pixel replacement to change contrast and brightness, histogram sliding and stretching, equalization, contouring, and thresholding of images and false coloring. This program is useful to identify and quantify fluorescing intensities of images within and around burned or damaged skin. Once quantified, fluorescing intensity values below a predetermined threshold value is set to represent areas which have deep burns, and values above a certain threshold represents shallow burns or unburned tissue. Thus, the computer is designed for quantitative image analysis, densitometry, image segments, digital substraction imagine, area measurements, and false coloring. An optical storage device is also provided; this is a write once read many times computer hardware optical disc storage system capable of storing large quantities of data on a library with 940 megabits of memory. This is useful because each processed image consumes about 250 K of memory in the computer.

A color monitor 36 (e.g., a Sony PVM 1271Q) is used to display the output of computer 28. Output from the image intensifier and camera 20 is monitored with monitor 38, e.g., a black and white Panasonic TR-930 which allows the operator to visually observe and monitor the fluorescence which the camera captures before processing in the computer. Information is passed from monitor to computer via black and white (B&W) signal cable. Hard copy from computer 28 is obtained using a laser printer 40 (Hewlett Packard Laser Jet Series II). A third monitor 42 is also provided, e.g., an NEC multisync 3-D color monitor to visually access the computer and software information and data. Color monitor 36 (Sony 8VM 1271Q) allows the user to observe pre processed and processed images in color. It is capable of receiving, via red green-blue-primary color cables, images processed from the computer, and capable of sending color signals to a video printer (44, Sony) via R_G_B primary color cables for color hard paper copies of the images. It is also capable of transferring images to a video cassette recorder (46, VCR) from the video printer via light analog input and output cables (LAI). This allows recording, via NTSC cable (standard Video Cable), the entire imaging process and data translation process on videotape.

Indocyanine Green Fluorimeter

Figure 4:
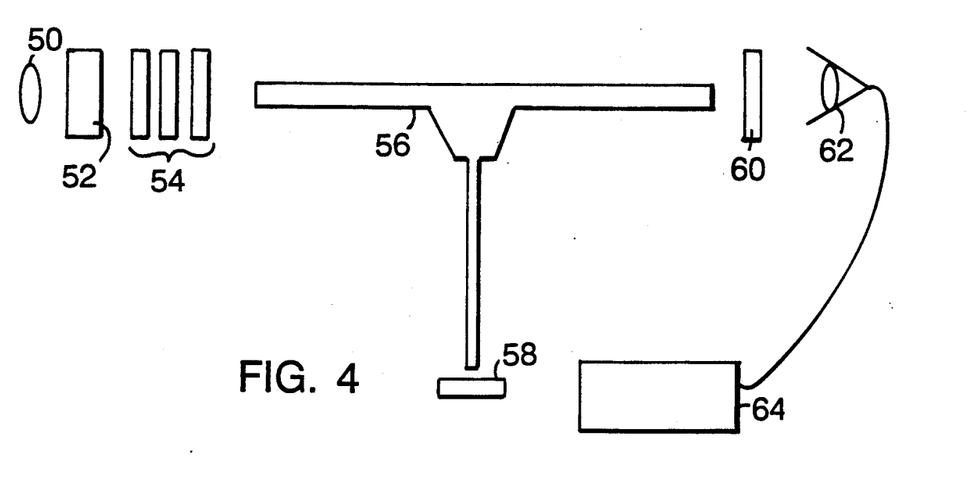
FIG. 4 is a diagrammatic representation of an indocyanine green fluorimeter.

Referring to FIG. 4, there is shown a basic system useful for collecting rat burn data to show that full from partial thickness burns can be distinguished on the basis of their fluorescence intensity after UV and IR excitation of intravenously administered indocyanine green.

A light source 50, is the same as that described above, using a handmade water container 52 which filters out infrared radiation above 2 microns wavelength. This prevents heat denaturation and overload of equipment. Filters 54 are the same as described for the above video imaging device. Bifurcated fiber 56 is provided to take filtered excitation radiation from source 50 and transmit it to a target 58, and to take the fluorescing radiation response from the target tissue and deliver it to a detector via a barrier filter 60, similar to that described above. A photomultiplier tube 62 (Hamamatsu #R829) is provided to detect, amplify, and quantify the photons fluorescing from the tissue target. A lock in amplifier 64 (Stanford Research Systems Dual Channel Lock In Amplifier #SR510) includes an electronic filter to eliminate background static (electrical noise) from the system, and amplify the signal from the photomultiplier tube for guantification of the fluorescence signal.

METHODS

The above described dual wavelength fluorescence fluorimeter and fluorescent videoimaging system are used generally as follows: A fluorescing vital dye excited by infrared light is injected into a mammal, and allowed to perfuse through viable skin via patent viable cutaneous circulation. The dye is then excited with either short or long wavelength radiation. The fluorescence of the vital dye is quantified either through fiberoptics and a photomultiplier tube (in the case of the fluorimeter), or via a videocamera and image processing computer (in the case of the videoimaging device).

We have found that the quantified fluorescence intensity is directly related to the cutaneous blood volume, and thus viablility of the observed tissue (skin). The intensity is inversely related to the thickness of the overlying burnt or necrotic tissue. The stronger or more intense the fluorescence, the more blood in the tissue, the thinner the burn, and the less the tissue is injured. The weaker or less intense the fluorescence, the less blood in the tissue, and the more tissue that is injured or burned. Since ultraviolet excitation excites vital dye near the surface of the skin, and infrared light excites vital dyes deeper in the tissue, various tissue depths can be examined for viability.

The recorded and quantified fluorescence of the target or burned tissue perfused with dye, is corrected for any autofluorescence of the tissue (from endogenous chromophores), by subtracting the fluorescence of target which occurs before injection of dye. Corrected burned or target tissue fluorescence values are then compared to normal tissue as fluorescence ratio's (FR). This fluorescence ratio relates to the relative blood volume, and thickness of the necrotic tissue in the target area, and is calculated as burn tissue fluorescence intensity (post dye minus pre dye injection) divided by normal tissue fluorescence intensity (post dye minus pre dye injection).

EXAMPLE 1

Indocyanine Green

Indocyanine green is injected intravenously into the patient to be analyzed. The dye enters the blood system and passes within capillaries which are adjacent and beneath the area of skin burn. The dye will not significantly pass into capillaries which are damaged by the burn. Prior to injection of this dye, one of the above described devices is used to determine natural or background fluorescence of the skin in the burnt area and in the adjacent unburnt skin. After injection, fluorescence is again detected, and the background level of fluorescence subtracted from that in the presence of the fluorescent dye. The ratio of fluorescence in the area of skin burn to unburnt skin is determined. Similarly, the ratio of fluorescence after excitation with ultraviolet or infrared light is determined.

EXAMPLE 2

Fiberoptic System

Figure 5:
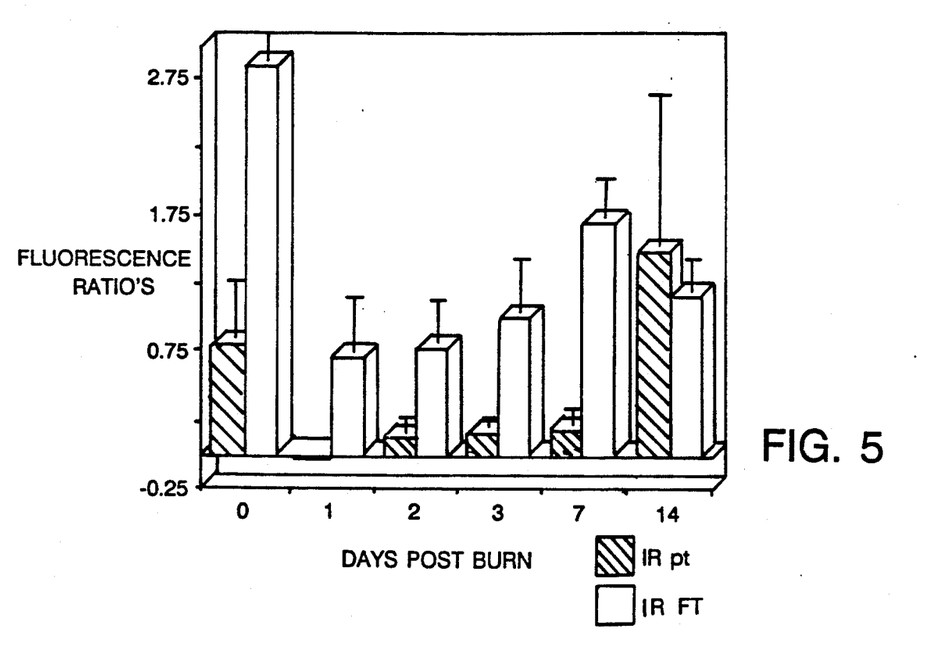
FIGS. 5 and 6 are graphical representations of fluorescence ratios with infrared and ultraviolet light, respectively.
Figure 6:
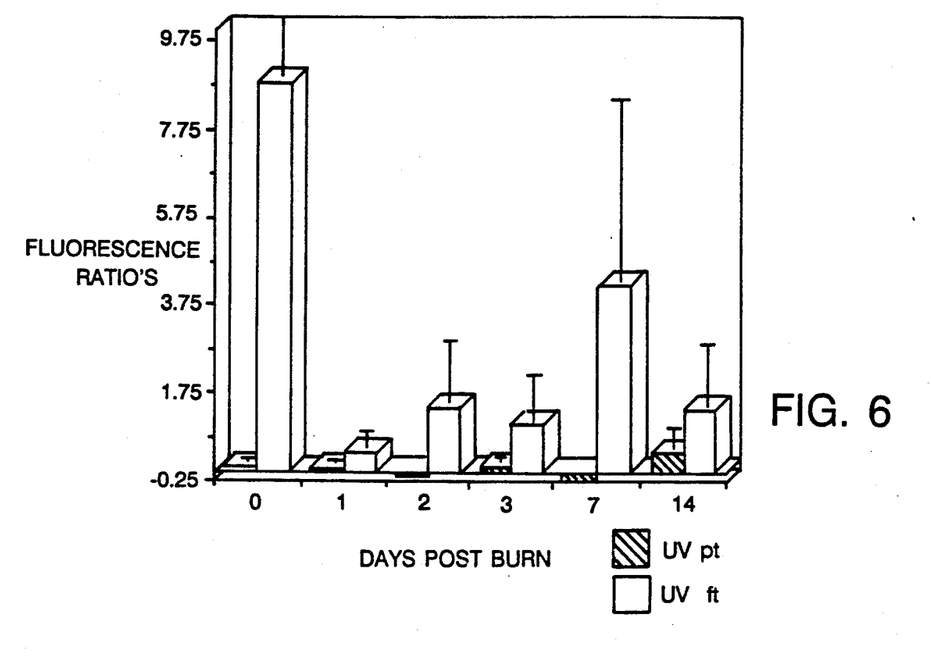

Referring to FIGS. 5 and 6, male hairless fuzzy rats (6-11 weeks old, weighing at least 250 grams) were selected for burns. Anesthesia was by use of inhaled anhydrous ether and intramuscular ketamine and xylazine prior to burning and injection of the indocyanbine green. The burns were induced with heated brass blocks heated to 100° C. in boiling water and applied to the skin for either 20 seconds for the full thickness burn, or 2 seconds for the partial thickness burn. The full thickness burn was placed on the right paraspinal area at least 3 cm cephalad to the partial thickness burn which was induced on the contralateral side. Normal unburned skin at the same level and on the contralateral side to the burn was used for controls. On day zero identical full and partial thickness burns were induced on the backs of 24 rats. Four rats were selected from this group on days 0, 1, 2, 3, 7 and 14 post burn for fluorescence studies.

In this rat model, the above fiberoptic system, with the particular characteristics described below, was used to determine the FR on certain days post burn wound induction. The fiberoptic fluorimeter is designed to emit two wavelengths and quantify indocyanine green infrared tissue fluorescence. Excitation light was produced by an ILC Technology R300-3 Xenon Lamp. Narrow band excitation filters interposed between the lamp and the bifurcated fiberoptic bundle (Fiberguide Industries) delivered the desired wavelength of light to the skin, (369 nm DF 39 Omega Optical Inc., or 780 nm DF 20 ESCO Industries). Light produced by fluorescence passed from the vasculature in the skin or eschar, through the fiberoptic fiber towards barrier filters (840 nm DF 20 Omega Optics, 850 nm DF 20 ESCO Industries) permitting transmission of near infrared IG fluorescent light while blocking light of lower or higher wavelengths. The intensity of the fluorescence was detected in the photomultiplier tube, and quantified through the lock in amplifier.

Background fluorescence readings were performed on burned and normal skin prior to injection of indocyanine green (10 mg/kg). Injections were performed under anesthesia, via the femoral vein. Indocyanine green infrared fluorescence intensity was quantified during one hour after injection and at 24 hours after intravenous bolus of indocyanine green. Immediately after the 24 hour post injection fluorescence assessment, the rates were sacrificed, and tissue from the burned sites sent for histopathology. The intensity of indocyanine green infrared fluorescence for both burn areas and their contralateral normal skin was evaluated on Days 0, 1, 2, 3, 7 and 14 post burn induction. Four previously noninjected burned rats were taken out of the original group of 24 and studied on each of these days. Fluorescence intensity for each type of burn were expressed as a ratio of burned to normal skin after subtracting out pre-indocyanine green background fluorescence values.

Certain FRs were found to represent either full or partial thickness wounds, as shown in the Figures. The graphs shown in FIGS. 5 and 6 represent some of the data collected from burned rats using this system. The first graph (FIG 5) is an example of infrared excitation of FT (full thickness) and PT (partial thickness) burns and the corresponding fluorescence ratios of the burned tissue to normal tissue. Whether excited by shallow penetrating UV or deep penetrating IR radiation, the full and partial thickness burns were distinguishable by their fluorescence ratios on days 0, 1, 2, 3, 7, and 14 post burn wound induction after injection of 10 mg/kg indocyanine green.

The fluorescence of indocyanine green in normal skin, partial thickness burns, and full thickness burns after excitation with ultraviolet light (369 nm, which fluoresces at 840 nm), and after excitation with infrared light (780 nm, which fluoresces at 850 nm), was determined on the aforementioned days post burn. Full thickness burns had a fluorescence intensity not significantly greater than that of normal skin lacking fluorescent dyes incorporated into capillaries. Partial thickness burns had a fluorescence intensity 2-3 fold greater than that of the background level, with both ultraviolet and infrared radiation.

EXAMPLE 3

Video Imaging

The following algorithm is applicable when indocyanine green is used as the vital fluorescing dye in the video imaging device (where +represents degrees of IR fluorescence intensity, with + + + +being the highest, − − −represents nil IR fluorescence):

|  | normal skin | superficial dermal burn | deep dermal burn | full thickness burn |
| --- | --- | --- | --- | --- |
| UV excitation: | + + + + | + + + − | + − − − | − − − − |
| IR excitation: | + + + + | + + + + | + + − − | − − − − |

Figure 3A:
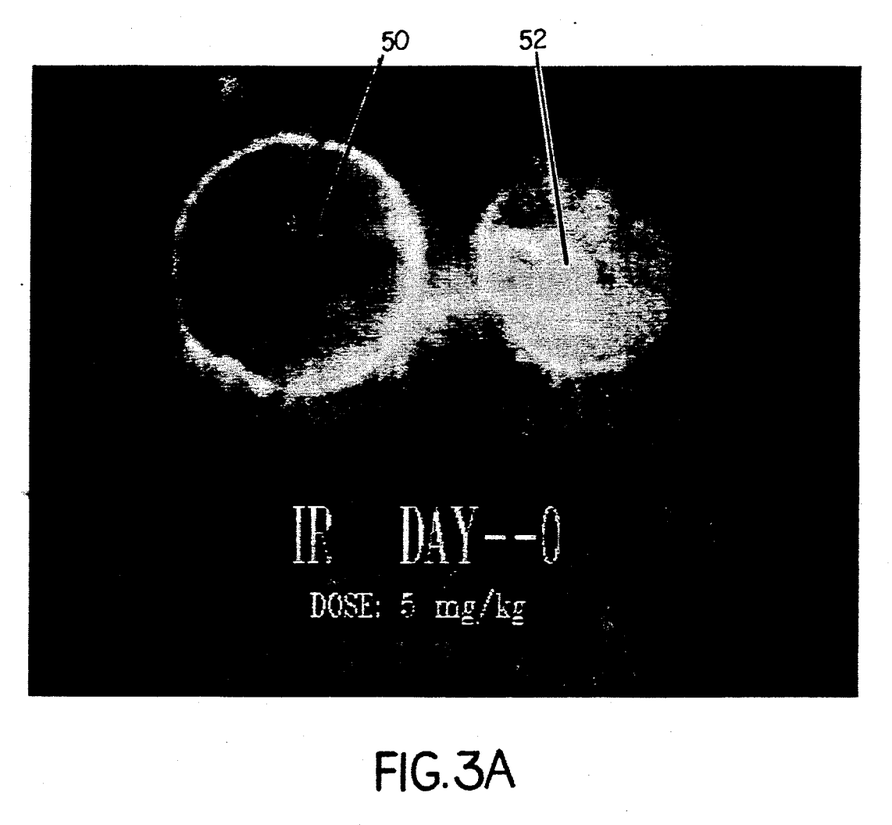
FIGS. 3a, b and c are photographs of images obtained with an image processing system.
Figure 3B:
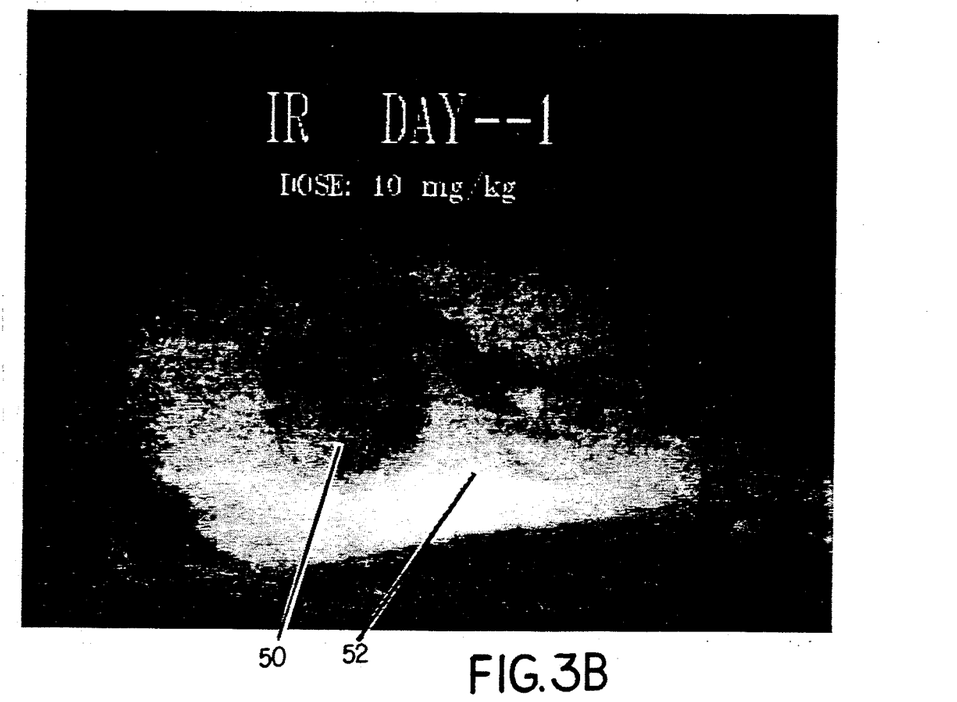
Figure 3C:
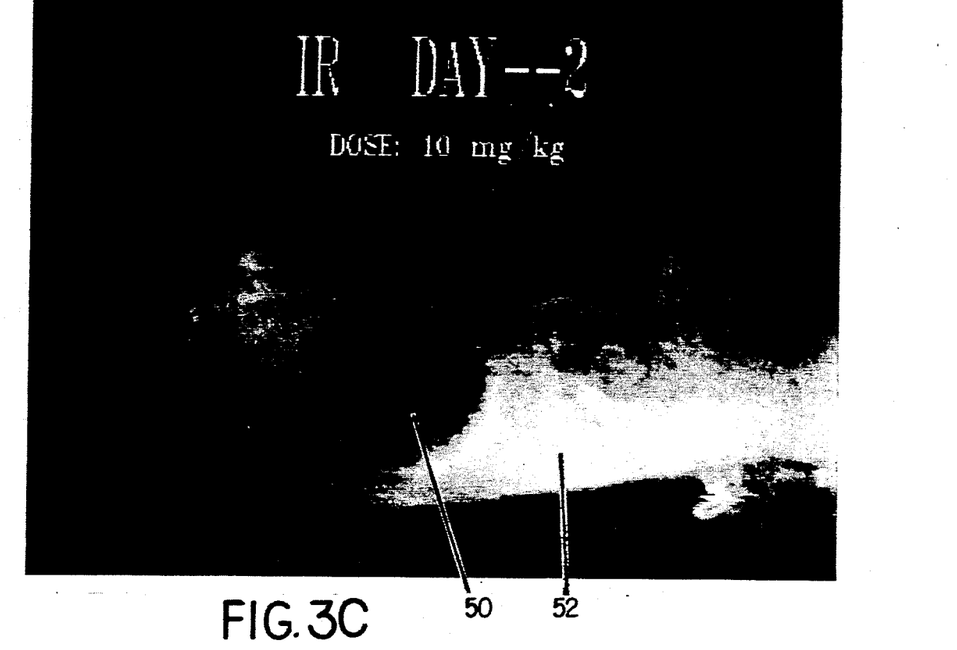

Referring to FIGS. 3a, b, and c, using video imaging system 10 described above, the 3 images shown in the figures were obtained with burns created as described in Example 2. Areas of full thickness burns (e.g., area 50) had little or no fluorescence compared to areas of unburned tissue (e.g., area 52). In each of these figures between 5 and 10 milligrams per kilogram of indocyanine green was injected, as described above, and fluorescence detected in the infrared range after excitation with infrared light. FIG. 3a shows the image a few hours after burning, whereas FIGS. 3b and 3c show the image 1 and 2 days, respectively, after burning. These data demonstrate that a full thickness burn can be detected within a few hours after burning. This allows immediate removal of the burned tissue and grafting of the burnt area, to provide rapid recovery of the burn area.

The video imaging technique can be used prior to removal of eschar, at the same time as removal of eschar, or after removal of eschar. Thus, it allows continuous monitoring of burn depth and the amount of eschar still to be removed. This permits a surgeon to excise eschar until only a few micron thickness remains, without damaging underlying viable tissue.

Eschar Removal

We have found that removal of burn eschar is readily achieved with a pulsed $CO_2$ laser. A conventional pulsed $CO_2$ laser is provided with a pulse width of less than 200 microseconds, preferably between 100 to 200 microseconds; at a fluence between 5.0 and 19 joules/$cm^2$; and at a repetition rate of delivery to one spot of tissue not greater than 50 pulses per second. Such a laser limits the zone of thermal damage to less than 150 microns in tissue subjacent to that excised, and allows removal of tissue from the surface of skin burns precisely, with an accuracy of tens of microns. The tissue is removed efficiently and blood loss prevented by hemostasis. Normal healing of the tissue, and normal skin graft take, is achieved. Burn tissue is excised by surface removal of an area exceeding about 0.5 $cm^2$. A tangential type of excision is used to remove the surface tissue, and to conserve viable structures.

EXAMPLE 4

Pulsed $CO_2$ Laser

Freshly excised burned (48 hour) and unburned swine skin was exposed to a pulsed $CO_2$ laser having parameters set as described above. The threshold radiant exposure per pulse for ablation in normal skin and eschar was 1.9 to 3.2 joules per centimeter square and 2.5 to 3.5 joules per centimeter square respectively. The operating radiant exposures for most efficient ablation was between 5.0 and 19 joules per centimeter square. At these fluences with a spot size of 1.9 mm, 0.00015 grams of tissue were ablated per pulse. Radiant exposures above 19 joules per centimeter square produced plasma, which decreased the efficiency of laser ablation. The heats of ablation for normal and burned skin was 2706 and 2416 joules per cubic centimeter of tissue ablated, respectively.

A mechanically scanned pulsed $CO_2$ laser was used for in vivo surface eschar excision. The laser performed bloodless excisions of 48 hour old full thickness burns on the backs of male hairless rats. Only visual feedback was needed to allow laser ablation to be stopped within microns of the viable underlying muscle fascia.

In partial thickness of laser excisions, the laser created a thermal damage of 85 microns over the fascia. Polymorphonuclear leucocytes and foreign body giant cells removed the denatured collagen within the laser created zone of thermal damage through day 7 post excision. By day 7, epithelial coverage of the laser created wounds was not significantly different from dermatome created wounds. Dermal collagen reformation was more vigorous in the healing laser created wounds on days 7, through 28. By day 35 post excision the two excisional modalities demonstrated no difference in the thickness of the new granulating dermis. At 42 days the two wounds were virtually indistinguishable histopathologically. There was no significant difference in area of the two wounds over 42 days.

The above video imaging system and pulsed $CO_2$ laser are useful in other applications. For example, the above video imaging system in combination with an infrared excited dye, e.g., indocyanine green, can be used to predict the viability of arterialized flaps, determine the degree of peripheral vascular disease, and delineate the margins of necrotic tissues and infarcted organs. The pulsed $CO_2$ laser described above is also useful for removal of the dye associated with a tattoo in the mid dermis or higher regions of the skin; for precise diepithelialization; for cosmetic surgery, for example, breast reconstructions; for surface surgery, for example, removal of moles and skin cancers; for internal organ removal, for example, conization; and for removal of cervical intraepithelial neoplasia.

Other embodiments are within the following claims.

We claim:

1. A method for determining the thickness of a skin burn in a a patient, comprising the steps of:
    administering a first fluorescent compound, which is excitable by infrared light, to said patient to cause said administered compound to enter one or more capillaries below and adjacent the skin burn;
    exciting said administered compound with infrared light; and
    detecting the amount of fluorescence of said excited compound caused by said infrared light at the skin burn and at unburned skin adjacent the skin burn; and calculating a ratio of the amount of fluorescence detected at the skin burn to the amount of fluorescence detected at the unburned skin as an indication of the thickness of the skin burn.

2. The method of claim 1, further comprising a step of detecting the amount of fluorescence caused by said infrared light at the skin burn and at the unburned skin adjacent the skin burn prior to administering said first fluorescent compound, and subtracting these levels of fluorescence from those levels of fluorescence detected after administering said fluorescent compound and prior to said step of calculating the ratio of the levels of fluorescence of said compound.

3. The method of claim 1 or claim 2, wherein a ratio of less than 0.4 indicates a full thickness skin burn.

4. The method of claim 1 or claim 2, further comprising a step of administering a second fluorescent compound, which may be the same as said first fluorescent compound, which is excitable by ultraviolet light, to said patient to cause said second fluorescent compound to enter one or more capillaries below and adjacent the skin burn;
    exciting said second fluorescent compound with ultraviolet light; and
    detecting the amount of fluorescence of said second fluorescent compound caused by said ultraviolet light at the skin burn and at unburned skin adjacent the skin burn; and calculating a ratio of the amount of detected fluorescence of said second compound at the skin burn to the amount of fluorescence detected at the unburned skin as an indication of the depth of the skin burn.

5. The method of claim 4 wherein said first fluorescent compound is indocyanine green.

6. The method of claim 5 wherein the ratio of the amount of detected fluorescence of said first fluorescent compound to the amount of detected second fluorescent compound in response to said infrared and ultraviolet light, respectively, is indicative of the depth of the skin burn.

7. The method of claim 4 wherein said first fluorescent compound is indocyanine green, and said second fluorescent compound is fluorescein.

8. The method of claim 7 wherein the ratio of the amount of detected fluorescence of said first fluorescent compound to the amount of detected second fluorescent compound in response to said infrared and ultraviolet light, respectively, is indicative of the depth of the skin burn.

9. The method of claim 7, wherein the step of detecting further comprises a step of measuring the amount of said first fluorescent compound and said second fluorescent compound with a dual wavelength fluorescence video imaging processing system.

10. The method of claim 1 or 2 wherein said first fluorescent compound is indocyanine green.

11. The method of claim 10, wherein the step of detecting further comprises a step of measuring the amount of said first fluorescent compound and said second fluorescent compound with a dual wavelength fluorescence video imaging processing system.

12. The method of claim 1, further comprising a step of removing the tissue from the skin burn after the step of detecting the amount of fluorescence, and further comprising a step of detecting the amount of fluorescence after said tissue removal.

13. The method of claim 12 wherein said step of tissue removal comprises excising the skin burn tissue with a pulsed $CO_2$ laser.

14. The method of claim 2, further comprising a step of removing the tissue from the skin burn after said calculating step and a step of detecting the amount of said fluorescence caused by said infrared light at the skin burn after said step of tissue removal.

* * * * *

UNITED STATES PATENT AND TRADEMARK OFFICE
CERTIFICATE OF CORRECTION

PATENT NO.  : 5,074,306

DATED       : Dec. 24, 1991

INVENTOR(S) : Howard A. Green, et al.

It is certified that error appears in the above-identified patent and that said Letters Patent is hereby corrected as shown below:

On the title page, item [75], should read as follows:

--Howard A. Green, West Roxbury; Richard R. Anderson, Somerville; John A. Parrish, Weston; Norman S. Nishioka, Wayland; Dominic Bua, Lynnfield, all of Mass.--.

Column 1, line 3, add the following:

"This invention was made with Government support under Contract #N00014-86-K-0117 awarded by the Office of Naval Research. The Government has certain rights in this invention."

Signed and Sealed this

Sixth Day of July, 1993

Attest:

MICHAEL K. KIRK

*Attesting Officer*   Acting Commissioner of Patents and Trademarks